US006558924B1

(12) United States Patent
Stahl et al.

(10) Patent No.: US 6,558,924 B1
(45) Date of Patent: May 6, 2003

(54) RECOMBINANT EXPRESSION OF INSULIN C-PEPTIDE

(75) Inventors: Stefan Stahl, Stockholm (SE); Mathias Uhlen, Masvager (SE); Per-Ake Nygren, Singelgrand (SE); Per Jonasson, Sodermannagatan (SE)

(73) Assignee: Creative Peptides Sweden AB, Djusholm (SE)

( * ) Notice: Subject to any disclaimer, the term of this patent is extended or adjusted under 35 U.S.C. 154(b) by 0 days.

(21) Appl. No.: 09/485,286

(22) PCT Filed: Aug. 7, 1998

(86) PCT No.: PCT/GB98/02382

§ 371 (c)(1),
(2), (4) Date: Feb. 7, 2000

(87) PCT Pub. No.: WO99/07735

PCT Pub. Date: Feb. 18, 1999

(30) Foreign Application Priority Data

Aug. 7, 1997 (GB) .............................. 9716790

(51) Int. Cl.$^7$ .................. C12N 15/00; C12N 15/17; C12N 15/63; A61K 38/28; C07K 14/62
(52) U.S. Cl. .................... 435/69.4; 435/69.1; 435/69.7; 435/252.3; 435/320.1; 435/325; 530/303; 530/350; 536/23.1; 536/23.5
(58) Field of Search .............................. 435/69.4, 69.1, 435/69.7, 70.1, 325, 252.3, 320.1; 530/350, 303; 536/23.1, 23.5

(56) References Cited

U.S. PATENT DOCUMENTS

| | | |
|---|---|---|
| 5,013,653 A | 5/1991 | Huston et al. |
| 5,130,236 A | 7/1992 | Hoffmann ................. 435/68.1 |
| 5,953,418 A | 9/1999 | Bock et al. .................. 380/20 |

FOREIGN PATENT DOCUMENTS

| | | |
|---|---|---|
| EP | 0 163 406 | 12/1985 |
| EP | 0 305 500 B1 | 3/1989 |
| EP | 0 327 522 | 8/1989 |
| EP | 0 431 926 A | 6/1991 |
| EP | 0 467 839 B1 | 1/1992 |
| EP | 0 591 524 A1 | 4/1994 |
| EP | 0 816 510 A1 | 1/1998 |
| FR | 2236845 | 2/1975 |
| GB | 2 068 971 A | 8/1981 |
| WO | WO 92/01707 | 2/1992 |

OTHER PUBLICATIONS

Bowie et al. Deciphering the Message in Protein Sequences: Tolerance to Amino Acid Substitutions. Science 247:1306–1310 (1990).*
Bork et al. Go hunting in sequence databases but what out for the traps. Trends in Genetics 12:425–427 (1996).*

Nilsson, J., et al., "Integrated production of human insulin and its C–peptide", Journal of Biotechnology, vol. 48, No. 3, Jul. 31, 1996, p. 241–250.
Lennick, M. et al., "High–level expression of alpha–human atrial natriuretic peptide from Multiple Joined Genes in *Escherichia coli*", Gene, vol. 61, No. 1, 1987, pp. 103–112.
Shen, S.–H., et al., "Multiple joined genes prevent product degradation in *Escherichia coli*", Proceedings of the National Academy of Sciences, vol. 81, 1984, pp. 4627–4631.
Geiger R., "Zur synthese von Peptiden mit Eigenschaften des Human–Proinsulin–C–Peptids (hC–Peptid),I", Chemische Berichte, vol. 106, 1973, pp. 188–192.
Nygren P., et al., "Analysis and Use of the Serum Albumin Binding Domains of Streptococcal Protein G", Journal of Molecular Recognition, vol. 1, No. 2, Apr. 1988, pp. 69–74.
Oberg, U., et al., "Intracellular production and renaturation from inclusion bodies of a scFv fragment fused to a serum albumin binding affinity tail", Progress in Biotechnology 9. EBC6: Proceedings of the 6$^{th}$ European Congress on Biotechnology, No. part 1, 1994, pp. 179–182.
Ido, Y. et al., "Prevention of vascular and neural dysfunction in a diabetic rats by C–peptide", Science, vol. 277, Jul. 25, 1997, pp. 563–566.
Johanssen, J. et al., "New insulins and other possible therapeutic approaches", Diabetologia, vol. 40, No. 3 suppl. 3, Oct. 1, 1997, pp. B89–B93.
David O. Irving, et al. *Expression of Repetitive Elements of RESA of Plasmodium Falciparum.* Technological Advances in Vaccine Development, pp. 97–105, 1988.
Hirokazu Ishikawa, et al. *Production of Human Calcitonin in Escherichia coli from Multmeric Fusion Protein.* Journal of Fermentation and Bioengineering, 82(2):140–144, 1996.
Per Jonasson, et al. *Single–step trypsin cleavage of a fusion protein to obtain human insulin and its C peptide.* Eur. J. Biochem. 236:656–661, 1996.
Per Jonasson, et al. *Gene fragment polymerization gives increased yields of recombinant human proinsulin C–peptide.* Gene, 210:203–210, 1998.
Tomas Kempe, et al. *Multiple–copy genes: production and modification of monomeric peptides from large multimeric fusion proteins.* Gene, 39:239–245, 1985.

(List continued on next page.)

*Primary Examiner*—Elizabeth Kemmerer
*Assistant Examiner*—Regina M. DeBerry
(74) *Attorney, Agent, or Firm*—Fish & Richardson P.C.

(57) ABSTRACT

The present invention provides a method of producing an insulin C-peptide, which comprises expressing in a host cell a multimeric polypeptide comprising multiple copies of the insulin C-peptide, and cleaving the expressed polypeptide to release single copies of the insulin C-peptide. Also provided are nucleic acid molecules, expression vectors and host cells, for use in such a method and the multimeric insulin C-peptide polypeptide expressed and cleaved in such a method.

41 Claims, 9 Drawing Sheets

OTHER PUBLICATIONS

Figure 2A:
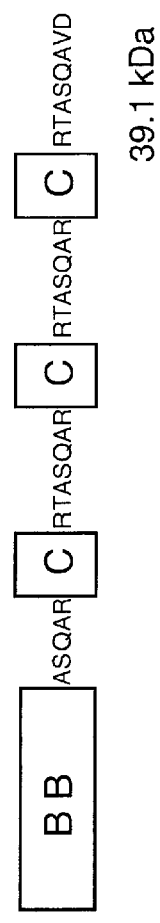

Charlotta Ljungquist, et al. *Immobilization and affinity purification of recombinant proteins using histidine peptide fusions*. Eur. J. Biochem., 186:563–569, 1989.

Etsuko Miyashita, et al. *High Level Production of a Peptide Hormone Analogue (Leu$^{13}$) Motilin in E. coli*. Biotechnology Letters 10(11):763–768, 1988.

Thien Ngoc Nguyen, et al. *De Novo Gene Assembly Using a Paramegnetic Solid Support*. Advances in Biomagnetic Separation, Eaton Publishing, Natick, MA, pp. 73–78.

Per–Ake Nygren, et al. *Engineering proteins to facilitate bioprocessing*. Tibtech 12:184–188, 1994.

Marco R. Oggioni, et al. *A host–vector system for heterlogous gene expression in Streptococcus gordonii*. Gene, 169:85–90, 1996.

G. Pozzi, et al. *Expression of M6 protein gene of Streptococcus pyogenes in Stretococcus gordonii after chromosomal integration and transcriptional fusion*. Res. Microbiol. 143:449–457, 1992.

S. Stahl, et al, *Solid–Phase Gene Assembly of Constructs Derived from the Plasmodium falciparum Malaria Blood–Stage Antigen Ag332*. Biotechniques 14:424–434, 1993.

S. Stahl, et al., *The use of Gene Fusions to Protein A and Protein G in Immunology and Biotechnology*. Pathologie Biologie 45 (1):66–76, 1997.

Stefan Stahl, et al. *A general strategy for polymerization, assembly, and expression of epitope–carrying peptides applied to the Plasmodium falciparum antigen Pf155/RESA*. Gene 89:187–193, 1990.

Akiko Takasuga, et al. *Efficient Production of a Small Peptide by Expression as a Multimeric Form Fused with the Dihydrofolate Reductase Affinity Handle*. J. Biochem. 112:652–657, 1992.

Ge Wei, et al. *Double C–Peptide Human Proinsulin*. Biochemisty and Molecular Biology International 35(1):37–46, 1995.

* cited by examiner

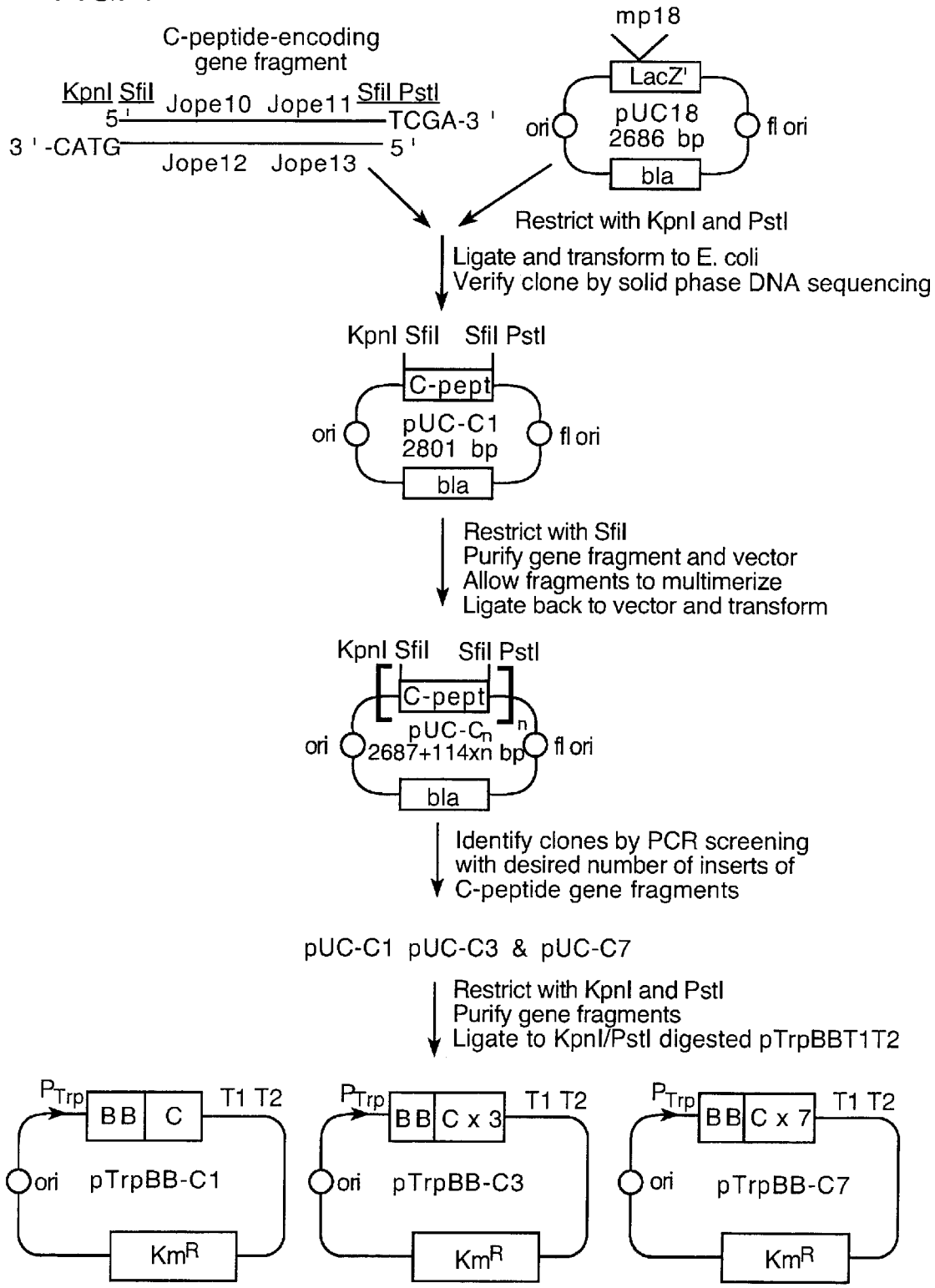

FIG. 2C   C-peptide = EAEDLQVGQVELGGGPGAGSLQPLALEGSLQ

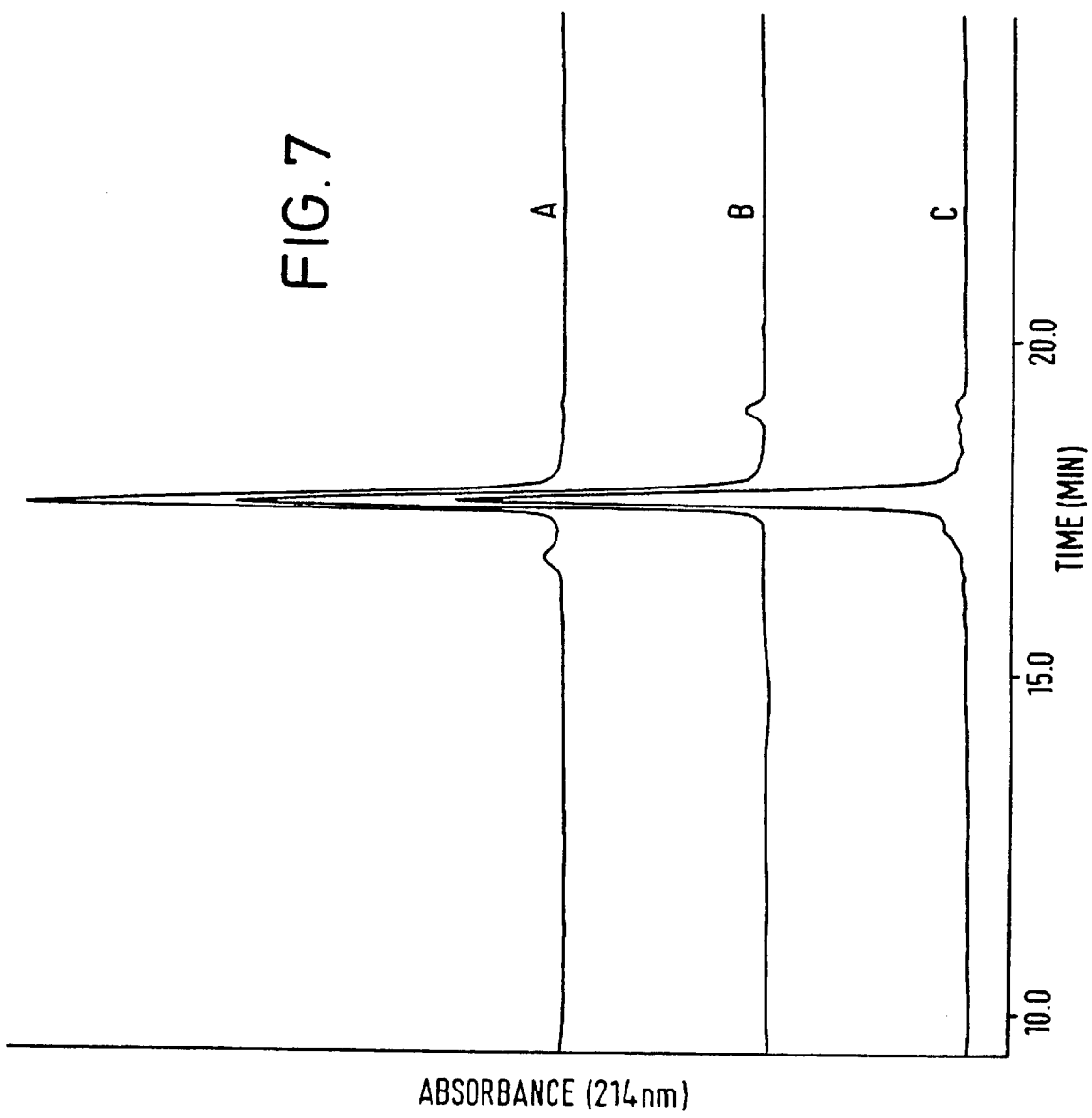

→ TripLE
MKAIFVLNAQHDEAVDANFDQFNKYGVSDYYKNLINNAKTVEGVKDLQAQVVESAKKARISEATDGLSDF
                ↑ BB

LKSQTPAEDTVKSIELAEAKVLANRELDKYGVSDYHKNLINNAKTVEGVKDLQAQVVESAKKARISEATD

GLSDFLKSQTPAEDTVKSIELAEAKVLANRELDKYGVSDYYKNLINNAKTVEGVKALIDEILAALPKTDT

YKLILNGKTLKGETTTEAVDAATARSFNFPILENSSSVPASQAREAEDLQVGQVELGGGPGAGSLQPLAL
                                            ↑ C1

EGSLQRTASQAREAEDLQVGQVELGGGPGAGSLQPLALEGSLQRTASQAREAEDLQVGQVELGGGPGAGS
   ↑ C2                                        ↑ C3

LQPLALEGSLQRTASQAREAEDLQVGQVELGGGPGAGSLQPLALEGSLQRTASQAREAEDLQVGQVELGG
      ↑ C4                                         ↑ C5

GPGAGSLQPLALEGSLQRTASQAREAEDLQVGQVELGGGPGAGSLQPLALEGSLQRTASQAREAEDLQVG
         ↑ C6                                          ↑ C7

QVELGGGPGAGSLQPLALEGSLQRTASQAVD

FIG. 8

SEQUENCE LISTING

<160> NUMBER OF SEQ ID NOS: 14

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 7
<212> TYPE: PRT
<213> ORGANISM: Artificial Sequence
<220> FEATURE:
<223> OTHER INFORMATION: Representative linker region

<400> SEQUENCE: 2

Arg Thr Ala Ser Gln Ala Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Representative linker region

<400> SEQUENCE: 3

Ala Ser Gln Ala Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Representative linker region

<400> SEQUENCE: 4

Arg Thr Ala Ser Gln Ala Val Asp
1               5

<210> SEQ ID NO 5
<211> LENGTH: 521
<212> TYPE: PRT
<213> ORGANISM: Artificial Sequence
<220> FEATURE:
<223> OTHER INFORMATION: Synthetically generated polypeptide

<400> SEQUENCE: 5

Met Lys Ala Ile Phe Val Leu Asn Ala Gln His Asp Glu Ala Val Asp
1               5                   10                  15

Ala Asn Phe Asp Gln Phe Asn Lys Tyr Gly Val Ser Asp Tyr Tyr Lys
            20                  25                  30

Asn Leu Ile Asn Asn Ala Lys Thr Val Glu Gly Val Lys Asp Leu Gln
        35                  40                  45

Ala Gln Val Val Glu Ser Ala Lys Lys Ala Arg Ile Ser Glu Ala Thr
    50                  55                  60

-continued

```
Asp Gly Leu Ser Asp Phe Leu Lys Ser Gln Thr Pro Ala Glu Asp Thr
 65                  70                  75                  80

Val Lys Ser Ile Glu Leu Ala Glu Ala Lys Val Leu Ala Asn Arg Glu
                 85                  90                  95

Leu Asp Lys Tyr Gly Val Ser Asp Tyr His Lys Asn Leu Ile Asn Asn
                100                 105                 110

Ala Lys Thr Val Glu Gly Val Lys Asp Leu Gln Ala Gln Val Val Glu
            115                 120                 125

Ser Ala Lys Lys Ala Arg Ile Ser Glu Ala Thr Asp Gly Leu Ser Asp
130                 135                 140

Phe Leu Lys Ser Gln Thr Pro Ala Glu Asp Thr Val Lys Ser Ile Glu
145                 150                 155                 160

Leu Ala Glu Ala Lys Val Leu Ala Asn Arg Glu Leu Asp Lys Tyr Gly
                165                 170                 175

Val Ser Asp Tyr Lys Asn Leu Ile Asn Asn Ala Lys Thr Val Glu
            180                 185                 190

Gly Val Lys Ala Leu Ile Asp Glu Ile Leu Ala Ala Leu Pro Lys Thr
            195                 200                 205

Asp Thr Tyr Lys Leu Ile Leu Asn Gly Lys Thr Leu Lys Gly Glu Thr
            210                 215                 220

Thr Thr Glu Ala Val Asp Ala Ala Thr Ala Arg Ser Phe Asn Phe Pro
225                 230                 235                 240

Ile Leu Glu Asn Ser Ser Val Pro Ala Ser Gln Ala Arg Glu Ala
                245                 250                 255

Glu Asp Leu Gln Val Gly Gln Val Glu Leu Gly Gly Pro Gly Ala
                260                 265                 270

Gly Ser Leu Gln Pro Leu Ala Leu Glu Gly Ser Leu Gln Arg Thr Ala
            275                 280                 285

Ser Gln Ala Arg Glu Ala Glu Asp Leu Gln Val Gly Gln Val Glu Leu
            290                 295                 300

Gly Gly Gly Pro Gly Ala Gly Ser Leu Gln Pro Leu Ala Leu Glu Gly
305                 310                 315                 320

Ser Leu Gln Arg Thr Ala Ser Gln Ala Arg Glu Ala Glu Asp Leu Gln
                325                 330                 335

Val Gly Gln Val Glu Leu Gly Gly Pro Gly Ala Gly Ser Leu Gln
            340                 345                 350

Pro Leu Ala Leu Glu Gly Ser Leu Gln Arg Thr Ala Ser Gln Ala Arg
            355                 360                 365

Glu Ala Glu Asp Leu Gln Val Gly Gln Val Glu Leu Gly Gly Pro
370                 375                 380

Gly Ala Gly Ser Leu Gln Pro Leu Ala Leu Glu Gly Ser Leu Gln Arg
385                 390                 395                 400

Thr Ala Ser Gln Ala Arg Glu Ala Glu Asp Leu Gln Val Gly Gln Val
                405                 410                 415

Glu Leu Gly Gly Gly Pro Gly Ala Gly Ser Leu Gln Pro Leu Ala Leu
            420                 425                 430

Glu Gly Ser Leu Gln Arg Thr Ala Ser Gln Ala Arg Glu Ala Glu Asp
            435                 440                 445

Leu Gln Val Gly Gln Val Glu Leu Gly Gly Pro Gly Ala Gly Ser
            450                 455                 460

Leu Gln Pro Leu Ala Leu Glu Gly Ser Leu Gln Arg Thr Ala Ser Gln
465                 470                 475                 480

Ala Arg Glu Ala Glu Asp Leu Gln Val Gly Gln Val Glu Leu Gly Gly
```

```
                485                 490                 495
Gly Pro Gly Ala Gly Ser Leu Gln Pro Leu Ala Leu Glu Gly Ser Leu
                500                 505                 510

Gln Arg Thr Ala Ser Gln Ala Val Asp
                515                 520
```

<210> SEQ ID NO 6
<211> LENGTH: 74
<212> TYPE: DNA
<213> ORGANISM: Artificial Sequence
<220> FEATURE:
<223> OTHER INFORMATION: Oligonucleotide for PCR

<400> SEQUENCE: 6

```
cggcctccca ggcccgcgaa gctgaggacc tgcaagttgg tcaggttgaa ctgggcggtg    60
gcccgggtgc aggc                                                      74
```

<210> SEQ ID NO 7
<211> LENGTH: 68
<212> TYPE: DNA
<213> ORGANISM: Artificial Sequence
<220> FEATURE:
<223> OTHER INFORMATION: Oligonucleotide for PCR

<400> SEQUENCE: 7

```
tctttgcagc cgctggcttt agaaggttct cttcagcgta cggcctccca ggccgtcgac    60
taactgca                                                             68
```

<210> SEQ ID NO 8
<211> LENGTH: 68
<212> TYPE: DNA
<213> ORGANISM: Artificial Sequence
<220> FEATURE:
<223> OTHER INFORMATION: Oligonucleotide for PCR

<400> SEQUENCE: 8

```
gggccaccgc ccagttcaac ctgaccaact tgcaggtcct cagcttcgcg ggcctgggag    60
gccggtac                                                             68
```

<210> SEQ ID NO 9
<211> LENGTH: 74
<212> TYPE: DNA
<213> ORGANISM: Artificial Sequence
<220> FEATURE:
<223> OTHER INFORMATION: Oligonucleotide for PCR

<400> SEQUENCE: 9

```
gttagtcgac ggcctgggag gccgtacgct gaagagaacc ttctaaagcc agcggctgca    60
aagagcctgc accc                                                      74
```

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 10

```
gcttccggct cgtatgtgtg                                                20
```

<210> SEQ ID NO 11
<211> LENGTH: 23

```
<212> TYPE: DNA
<213> ORGANISM: Artificial Sequence
<220> FEATURE:
<223> OTHER INFORMATION: Oligonucleotide for PCR

<400> SEQUENCE: 11
aaagggggat gtgctgcaag gcg                                            23

<210> SEQ ID NO 12
<211> LENGTH: 41
<212> TYPE: DNA
<213> ORGANISM: Artificial Sequence
<220> FEATURE:
<223> OTHER INFORMATION: Oligonucleotide for PCR

<400> SEQUENCE: 12 cccctgcag ctcgagcgcc tttaacctgt tttggcggat g                         41

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide for PCR

<400> SEQUENCE: 13
ccccaagctt agagtttgta gaaacgc                                        27

<210> SEQ ID NO 14
<211> LENGTH: 4646
<212> TYPE: DNA
<213> ORGANISM: Artificial Sequence
<220> FEATURE:
<223> OTHER INFORMATION: Expression vector

<400> SEQUENCE: 14
gcggccgcta attcatgctg tggtgtcatg gtcggtgatc gccagggtgc cgacgcgcat     60
ctcgactgca cggtgcacca atgcttctgg cgtcaggcag ccaatcggaa gctgtggtat    120
ggctgtgcag gtcgtaaatc actgcataat tcgtgtcgct caaggcgcac tcccgttctg    180
gataatgttt tttgcgccga catcataacg gttctggcaa atattctgaa atgagctgtt    240
gacaattaat catcgaacta gttaactagt acgcaagttc acgtaaaaag ggtatctaga    300
attatgaaag caattttcgt actgaatgcg caacacgatg aagccgtaga cgcgaatttc    360
gaccaattca acaaatatgg agtaagtgac tattacaaga atctaatcaa caatgccaaa    420
actgttgaag gcgtaaaaga ccttcaagca caagttgttg aatcagcgaa gaaagcgcgt    480
atttcagaag caacagatgg cttatctgat ttcttgaaat cacaaacacc tgctgaagat    540
actgttaaat caattgaatt agctgaagct aaagtcttag ctaacagaga acttgacaaa    600
tatggagtaa gtgactatca agaacctaa tcaacaatg ccaaaactgt tgaaggtgta    660
aaagacttc aagcacaagt tgttgaatca gcgaagaaag cgcgtatttc agaagcaaca    720
gatggcttat ctgatttctt gaaatcacaa acacctgctg aagatactgt taaatcaatt    780
gaattagctg aagctaaagt cttagctaac agagaacttg acaaatatgg agtaagtgac    840
tattacaaga acctaatcaa caatgccaaa actgttgaag gtgtaaaagc actgatagat    900
gaaattttag ctgcattacc taagactgac acttacaaat taatccttaa tggtaaaaca    960
ttgaaaggcg aaacaactac tgaagctgtt gatgctgcta ctgcaagatc tttcaatttc   1020
cctatcctcg agaattcgag ctcggtaccg gcctcccagg cccgcgaagc tgaggacctg   1080
```

```
caagttggtc aggttgaact gggcggtggc ccgggtgcag gctctttgca gccgctggct    1140
ttagaaggtt ctcttcagcg tacggcctcc caggcccgcg aagctgagga cctgcaagtt    1200
ggtcaggttg aactgggcgg tggcccgggt gcaggctctt tgcagccgct ggctttagaa    1260
ggttctcttc agcgtacggc ctcccaggcc cgcgaagctg aggacctgca agttggtcag    1320
gttgaactgg gcggtggccc gggtgcaggc tctttgcagc cgctggcttt agaaggttct    1380
cttcagcgta cggcctccca ggcccgcgaa gctgaggacc tgcaagttgg tcaggttgaa    1440
ctgggcggtg gcccgggtgc aggctctttg cagccgctgg ctttagaagg ttctcttcag    1500
cgtacggcct cccaggcccg cgaagctgag gacctgcaag ttggtcaggt tgaactgggc    1560
ggtggcccgg gtgcaggctc tttgcagccg ctggctttag aaggttctct tcagcgtacg    1620
gcctcccagg cccgcgaagc tgaggacctg caagttggtc aggttgaact gggcggtggc    1680
ccgggtgcag gctctttgca gccgctggct ttagaaggtt ctcttcagcg tacggcctcc    1740
caggcccgcg aagctgagga cctgcaagtt ggtcaggttg aactgggcgg tggcccgggt    1800
gcaggctctt tgcagccgct ggctttagaa ggttctcttc agcgtacggc ctcccaggcc    1860
gtcgactaac tgcagctcga gcgcttaact gttttggcgg atgagagaag attttcagcc    1920
tgatacagat taaatcagaa cgcagaagcg gtctgataaa acagaatttg cctggcggca    1980
gtagcgcggt ggtcccacct gacccatgc cgaactcaga agtgaaacgc cgtagcgccg    2040
atggtagtgt ggggtctccc catgcgagag tagggaactg ccaggcatca ataaaaacga    2100
aaggctcagt cgaaagactg ggcctttcgt tttatctgtt gtttgtcggt gaacgctctc    2160
ctgagtagga caaatccgcc gggagcggat ttgaacgttg cgaagcaacg gcccggaggg    2220
tggcgggcag gacgcccgcc ataaactgcc aggcatcaaa ttaagcagaa ggccatcctg    2280
acggatggcc tttttgcgtt tctacaaact ctaagctttg gtgcagggg gggggggaaa    2340
gccacgttgt gtctcaaaat ctctgatgtt acattgcaca agataaaaat atatcatcat    2400
gaacaataaa actgtctgct tacataaaca gtaatacaag gggtgttatg agccatattc    2460
aacgggaaac gtcttgctcg aggccgcgat taaattccaa catggatgct gatttatatg    2520
ggtataaatg ggctcgcgat aatgtcgggc aatcaggtgc gacaatctat cgattgtatg    2580
ggaagcccga tgcgccagag ttgtttctga acatggcaa aggtagcgtt gccaatgatg    2640
ttacagatga gatggtcaga ctaaactggc tgacggaatt tatgcctctt ccgaccatca    2700
agcattttat ccgtactcct gatgatgcat ggttactcac cactgcgatc cccgggaaaa    2760
cagcattcca ggtattagaa gaatatcctg attcaggtga aaatattgtt gatgcgctgg    2820
cagtgttcct gcgccggttg cattcgattc ctgttgtaa ttgtcctttt aacagcgatc    2880
gcgtatttcg tctcgctcag gcgcaatcac gaatgaataa cggtttggtt gatgcgagtg    2940
attttgatga cgagcgtaat ggctggcctg ttgaacaagt ctggaaagaa atgcataaac    3000
ttttgccatt ctcaccggat tcagtcgtca ctcatggtga tttctcactt gataacctta    3060
tttttgacga ggggaaatta ataggttgta ttgatgttgg acgagtcgga atcgcagacc    3120
gataccagga tcttgccatc ctatggaact gcctcggtga gttttctcct tcattacaga    3180
aacggctttt tcaaaaatat ggtattgata atcctgatat gaataaattg cagtttcatt    3240
tgatgctcga tgagtttttc taatcagaat tggttaattg gttgtaacac tggcagagca    3300
ttacgctgac ttgacgggac ggcggctttg ttgaataaat cgaactttg ctgagttgaa    3360
ggatcagatc acgcatcttc ccgacaacgc agaccgttcc gtggcaaagc aaaagttcaa    3420
aatcaccaac tggtccggat cccggtgcct cactgattaa gcattggtaa ctgtcagacc    3480
```

```
aagtttactc atatatactt tagattgatt taaaacttca tttttaattt aaaaggatct    3540
aggtgaagat ccttttgat aatctcatga ccaaaatccc ttaacgtgag ttttcgttcc    3600
actgagcgtc agaccccgta gaaaagatca aaggatcttc ttgagatcct tttttctgc    3660 gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
atactgtcct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacgaggga gcttccaggg ggaaacgcct    4140
ggtatcttta tagtcctgtc gggtttcgcc acctctgact tgagcgtcga tttttgtgat    4200
gctcgtcagg ggggcggagc ctatggaaaa acgaacgcaa cgcggccttt ttacggttcc    4260
tggccttttg ctggcctttt gctcacatgt tctttcctgc gttatcccct gattctgtgg    4320
ataaccgtat taccgccttt gagtgagctg ataccgctcg ccgcagccga acgaccgagc    4380
gcagcgagtc agtgagcgag gaagcggaag agcgcccaat acgcaaaccg cctctccccg    4440
cgcgttggcc gattcattaa tgcagctggc acgacaggtt tcccgactgg aaagcgggca    4500
gtgagcgcaa cgcaattaat gtgagttagc tcactcatta ggcaccccag gctttacact    4560
ttatgcttcc ggctcgtatg ttgtgtggaa ttgtgagcgg ataacaattt cacacaggaa    4620
acagctatga ccatgattac gaatta                                         4646
```

RECOMBINANT EXPRESSION OF INSULIN C-PEPTIDE

RELATED APPLICATION

This application claims priority to British Application No. 9716790.2, filed Aug. 7, 1997, the content of which is incorporated herein by reference.

The present invention relates to the production of insulin C-peptide from recombinant DNA molecules comprising multimeric copies of a gene sequence encoding said insulin C-peptide.

Insulin is a protein hormone involved in the regulation of blood sugar levels. Insulin is produced in the liver as: its precursor proinsulin, consisting of the B and A chains of insulin linked together via a connecting C-peptide (hereinafter this C-peptide derived from the proinsulin molecule is referred to as "insulin C-peptide"). Insulin itself is comprised of only the B and A chains. Several recent studies indicate that the C-peptide has a clinical relevance (Johansson et al., Diabetologia (1992) 35, 121–128 and J. Clin. Endocrinol. Metab. (1993) 77, 976–981). In patients with type 1 diabetes, who lack endogenous C-peptide, administration of the peptide improves renal function, stimulates barrier function (Johansson et al., 1992 and 1993 supra).

Although not yet widely recognised, there is a growing awareness in the medical field,of a therapeutic utility for the insulin C-peptide. Accordingly, there is a need for a method for the ready synthesis of insulin C-peptides, economically and efficiently. Whilst methods for the chemical synthesis of peptides, e.g. by stepwise addition of amino acids on a solid support, are now well developed, they remain, despite automation, time-consuming and, more significantly, costly to perform, and may also be limited in terms of the maximum peptide length economically and reliably synthesisable. As an alternative, methods for peptide production by expression of recombinant DNA have been developed, although these too are not without their drawbacks e.g. in terms of yield.

Current production schemes for insulin C-peptide are based on the processing of proinsulin$_1$ the precursor molecule for insulin and C-peptide, normally by the use of trypsin and carboxypeptidase B (Nilsson et al., (1996), J. Biotechnol. 48, 241–250); Jonasson et al., (1996) Eur. J. Biochem. 236, 656–661). Proinsulin was produced as a fusion protein that was capable of expression at high levels in *E. coli*, and the fusion protein was engineered in such a way that the fusion partner could be cleaved off simultaneously with the processing of proinsulin to insulin and C-peptide. Proinsulin was produced as a fusion protein with ZZ, a synthetic affinity fusion tag derived from staphylococcal protein A which binds IgG (Immuno-globulin) (Nilsson et al., (1987) Prot. Eng. 1, 107–113). This fusion tag was selected due to its stability to proteolysis, its IgG-binding capacity, its high expression levels and solubilizing properties. The chosen production strategy allowed the use of an affinity tag for efficient purification, after solubilization of inclusion bodies and subsequent renaturation, without the inclusion of additional unit operations for cleavage and removal of the ZZ affinity tag. The tag was demonstrated to be simultaneously cleaved off with the trypsin/carboxypeptidase B digestion of proinsulin to insulin and C-peptide. However, production of small peptides via the expression of large fusion proteins generally gives rather low yields, as the final product constitutes only a small part of the expressed gene product.

Shen in Proc. Natl. Acad. Sci. USA, 81, 4627–4631, 1984 describes a method for preparing human proinsulin by expression of a fused or unfused gene product comprising multiple tandemly linked copies of the proinsulin polypeptide domain. This gene product can be cleaved into single proinsulin units by cyanogen bromide treatment. It is proposed that human insulin can be prepared by cleavage of the proinsulin units with trypsin/carboxypeptidase. However, the problem of improving the yield of insulin C-peptide is not addressed.

There remains, therefore, a need for a recombinant expression method which improves the yield of insulin C-peptide, as an unfused product. The present invention addresses this need.

The present invention seeks to improve on existing methods for recombinant expression of peptides and essentially is based on the concept of increasing the amount of expressed target peptide (in this case an Insulin C-peptide) by expressing, as a single gene product, a multimer (i.e. a multimeric polypeptide) having multiple copies of the target peptide (insulin C-peptide), and then cleaving such a multimeric gene product (i.e. the multimeric polypeptide) to release the target peptide as individual monomer units.

In one aspect, the present invention thus provides a method of producing an insulin C-peptide, which comprises expressing in a host cell a multimeric polypeptide comprising multiple copies of a said insulin C-peptide, and cleaving said expressed polypeptide to release single copies of the insulin C,-peptide (i.e. to release the insulin C-peptide monomers from the multimer).

The multimeric polypeptide (gene product) is encoded by a genetic construct (in other words a nucleic acid molecule) comprising multiple copies of a nucleotide sequence encoding an insulin C-peptide. The multiple copies, or repeats, are linked in the construct in such a manner that they are transcribed and translated together into a single, multimeric gene product (i.e. a multimeric polypeptide) i.e. in "read-through format" e.g. the multiple nucleotide sequences are linked in matching reading frame in the construct. In essence, the genetic construct (nucleic acid molecule) advantageously comprises a concatemer of the insulin C-peptide encoding nucleotide sequence. Preferably, the genetic construct comprises tandem copies of the encoding nucleotide sequence. Such a genetic construct is thus prepared and is then introduced into a host cell in a standard manner, and expressed. The expressed gene product (polypeptide) may then be recovered and cleaved to release the insulin C-peptide monomers.

In a further aspect the invention thus provides a method for producing an insulin C-peptide, which comprises culturing a host cell containing a nucleic acid molecule comprising multiple copies of a nucleotide sequence encoding a said insulin C-peptide, under conditions whereby the multimeric polypeptide of said nucleic acid molecule is expressed, and cleaving said expressed polypeptide to release single copies of said insulin C-peptide.

As used herein the term "multiple" or "multimeric" refers to two or more copies of an insulin C-peptide or the nucleotide sequence which encodes it, preferably 2 to 50, 2 to 30 or 2 to 20, more preferably 2 to 15, or 2 to 10. Further exemplary ranges also include 3 to 20, 3 to 15 or 3 to 10.

Conveniently, the construct comprises 3 or more copies e.g. 3 to 7, or 5 to 7, copies of the nucleotide sequence encoding a insulin C-peptide. Ranges of 7 or more, for example 7 to 30, 7 to 20 or 7 to 15 may also be useful.

The term "insulin C-peptide" as used herein includes all forms of insulin C-peptide, including native or synthetic peptides. Such insulin C-peptides may be human peptides, or may be from other animal species and genera, preferably mammals. Thus variants and modifications of native insulin C-peptide are included as long as they retain insulin C-peptide activity. The insulin C-peptides may be expressed in their native form, i.e. as different allelic variants as they appear in nature in different species or due to geographical variation etc., or as functionally equivalent variants or derivatives thereof, which may differ in their amino acid sequence, for example by truncation (e.g. from the N- or C-terminus or both) or other amino acid deletions, additions or substitutions. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc. Thus, functionally equivalent variants or derivatives of native insulin C-peptide sequences may readily be prepared according to techniques well known in the art, and include peptide sequences having a functional, e.g. a biological, activity of a native insulin C-peptide. Thus, in terms of such activities, for example, insulin C-peptide is known to have an activity in stimulating $Na^+K^+ATPase$, which may underlie various of the therapeutic activities reported for C-peptide, e.g. in the treatment or diabetes or in the treatment or prevention of diabetic complications such as diabetic neuropathy, nephropathy and retinopathy. Fragments of native or synthetic insulin C-peptide sequences may also have the desirable functional properties of the peptide from which they derive and are hence also included. Mention may be made in particular of the insulin C-peptide fragments described by Wahren et al., in WO98/13384. All such analogues, variants, derivatives or fragments of insulin C-peptide are especially included in the scope of this invention, and are subsumed under the term "an insulin C-peptide".

Conveniently, the native human insulin C-peptide may be used and is shown in FIG. 2C (SEQ ID. NO. 1.)

In a further preferred embodiment of the method according to the invention, the gene construct will additionally comprise a sequence which encodes a fusion partner (fusion tag) e.g. which is capable of binding to matrices used during processing of the product of gene expression.

The term "fusion partner" refers to any protein or peptide molecule or derivative or fragment thereof which is translated contiguously with the insulin C-peptide whose properties can be utilised in the further processing of the expressed fusion product.

The interaction between the fusion partner and the matrix may be based on affinity, chelating peptides, hydrophobic or charged interactions or any other mechanism known in the art. Conveniently, the fusion partner is one of a pair of affinity binding partners or ligands e.g. a protein, polypeptide or peptide sequence capable of selectively or specifically binding to or reacting with a ligand. Suitable fusion partners include for example streptococcal protein G and staphylococcal protein A and derivatives thereof, β-galactosidase, glutathione-S-transferase and avidin or streptavidin, or a fragment or derivative of any aforesaid protein, which have strong affinities with immunoglobulin G, substrate analogues or antibodies and biotin respectively. Such interactions can be utilised to purify the fused protein product from a complex mixture. The ZZ fragment of protein A (see Nilsson et al., supra) is an example of a protein fragment which may be used. Histidine peptides can be used as fusion partners as they bind to metal ions e.g. $Zn^{2+}$, $Cu^{2+}$ or $Ni^{2+}$ and elution may be performed by lowering the pH or with EDTA (Ljungquist et al. (1989) Eur. J. Biochem. 186, 563–569). Particularly preferred polypeptide fusion partners are a 25 kDa serum albumin binding region (BB) derived from streptococcal protein G (SpG) (Nygren et al. (1988) J. Mol. Recogn. 1 69–74) or other SpG-derived albumin binding tags (Stahl and Nygren (1997) Path. Bio. 45, 66–76). Öberg et al., describe an expression vector, pTrp BB, (SEQ ID NO. 14) suitable for insertion of gene fragments for expression of a desired product as a fusion protein with BB (Proceedings of the 6th European Congress on Biotechnology, 1994, 179–182). These fusion partners have a strong affinity to albumin and therefore purification of the expressed fusion protein can be based on ligand affinity chromatography e.g. using a column charged with albumin. The albumin is preferably immobilised on a solid support.

Any convenient means may be used to achieve the cleavage step, i.e. the cleavage of the monomeric insulin C-peptides from the multimeric polypeptide i.e. from the expressed gene product, and optionally from the fusion partner if present. Conveniently, this may be achieved using enzymes. Preferably, the initial product of gene expression, i.e. the multimeric polypeptide or the fusion product or fusion protein, which comprises the fusion partner and multiple copies (monomers) of the insulin C-peptide, is cleaved by one or more proteolytic enzymes in a single process step to yield unfused single copies of the insulin C-peptide. A combined treatment with trypsin and carboxypeptidase B (e.g. from bovine, porcine or other sources) is a particularly preferred method of obtaining the desired cleavage products. Trypsin cleaves the proteins C-terminally of each arginine residue and carboxypeptidase B removes the C-terminal arginine present on each peptide after trypsin digestion. Conditions for achieving proteolytic cleavage are well known in the art, as are a range of other suitable proteolytic enzymes such as Subtilisin (including mutants thereof), Enterokinase, Factor Xa, Thrombin, IgA protease, Protease 3C, and Inteins. It has been found, for example, that incubation of the expressed gene product with the proteolytic enzymes (e.g. trypsin and carboxypeptidase B) for 60 minutes is sufficient for complete processing of the expressed protein. Conveniently, 5 minutes incubation time may be sufficient for adequate processing of the fusion protein such that no fusion or multimeric protein is detectable by conventional SDS PAGE. Alternatively, the initial product of gene expression may be cleaved by chemical reagents such as CNBr, hydroxylamine or formic acid.

Depending on the precise nature of the insulin C-peptide and nucleic acid molecule (genetic construct) used, the cleavage sites e.g. for proteolysis may be present naturally, or they may be introduced by appropriate manipulation of the genetic construct using known techniques e.g. site-directed mutagenesis, ligation of appropriate cleavage site-encoding nucleotide sequences etc.

Conveniently, the multimeric expressed polypeptide may include a linker region i.e. a linker residue or peptide incorporating or providing a cleavage site. Advantageously, the cleavage site comprises a cleavable motif recognised and cleaved by a proteolytic enzyme. Linker regions may be incorporated between each "monomer" peptide in the multimeric construct, and/or optionally also between the fusion partner if present and a monomer peptide. Advantageously, each monomer peptide may be tandemly arranged with a linker region. Advantageously, the insulin C-peptide monomers in the multimer are flanked by appropriate linker sequences to ensure cleavage and release of insulin C-peptide free of any linker region residues. The linker region may comprise from 1 to 15 e.g. 1 to 12 or 1 to 10 amino residues, although the length is not critical and may be selected for convenience or according to choice. Linker regions of from 1 to 8, e.g. 1, 5 and 7 may be convenient. The individual linker region within each construct may be the same or different, although for convenience they are generally the same. Thus, for example, for cleavage by the combination of trypsin and carboxypeptidase B, linkers beginning or terminating in arginine residues may be provided.

An alternative linker may comprise the amino acid lysine, either solely or as part of a longer sequence and may also be cleaved by the trypsin/carboxypeptidase B combination.

For inclusion between insulin C-peptide monomers, such linkers may advantageously start with and terminate in such a cleavage site e.g. an arginine residue at both their N and C termini, to ensure release of an insulin, C-peptide monomer without any additional amino acids. For inclusion between the fusion partner and/or at the end of the insulin C-peptide multimer, a single cleavage site (e.g. Arg) may be present at the appropriate terminus of the linker, (or correspondingly at an appropriate site for cleavage, depending on the precise linker sequence and cleavage enzymes used).

Exemplary representative linker regions include -RTASQAR- (SEQ ID NO. 2) for inclusion between C-peptide monomers, -ASQAR- (SEQ ID NO. 3) between the fusion partner and a C-peptide multimer and -RTASQAVD (SEQ ID NO. 4) at the end of the multimer.

As mentioned above, standard methods well-known in the art may be used for the introduction of linker sequences.

A further aspect of the present invention is a nucleic acid molecule comprising multiple copies of a nucleotide sequence encoding an insulin C-peptide, wherein said nucleic acid molecule encodes a multimeric polypeptide capable of being cleaved to yield single copies of said insulin C-peptide.

Alternatively viewed, this aspect of the invention can be seen to provide a nucleic acid molecule comprising a concatemer of a nucleotide sequence encoding an insulin C-peptide.

The various aspects of the invention set out above (and below) include embodiments where the multimeric polypeptide (gene product) does not include both an insulin A and an insulin B peptide, or where the nucleic acid molecule does not encode both an insulin A and B peptide. More particularly, in such embodiments, where the number of copies of insulin C-peptide in the multimeric polypeptide, or encoded by the nucleic acid molecule, is two, the multimeric polypeptide does not include, or the nucleic acid molecule does not encode, both insulin A and B peptides.

In a particularly preferred embodiment of the invention, the nucleic acid molecule will additionally comprise a nucleotide sequence which encodes a fusion partner which assists in the further processing of the encoded multimeric polypeptide e.g. which is useful for purification of the expressed protein product. The gene encoding the fusion partner will be in the correct position and orientation to be translated together with the multiple copies of the insulin C-peptide to form, initially, a single fused peptide. Suitable fusion proteins are discussed above.

Advantageously, the nucleic acid molecule will also comprise one or more nucleotide sequences encoding linker regions comprising cleavage sites, as discussed above.

As exemplary of nucleic acid molecules according to the invention may thus be mentioned those encoding a polypeptide of Formula I)

$$H_2N\text{-}A\text{-}(C\text{—}X)_n\text{—}COOH \tag{I}$$

wherein
C is an insulin C-peptide;
A is a bond, or a group F, wherein F is a fusion partner, or a group —(F—X)—;
X is a linker region comprising at least one cleavage site, each X being the same or different; and
n is an integer of 2 to 50.

This aspect of the invention includes an embodiment wherein Formula (I) includes the proviso that when n=2, said polypeptide (I) does not comprise an insulin A and B chain.

Insulin C-peptides (group C), fusion partners (group F) and linker regions (group X) may be as defined above. Likewise n may be as defined above in relation to the terms "multiple" and "multimeric".

The nucleic acid molecule or genetic construct useful in the methods of the invention will preferably contain a suitable regulatory sequence which will control expression in the host cell. Such regulatory or expression control sequences include, for example, transcriptional (e.g. promoter-operator regions, ribosomal binding sites, termination stop sequences, enhancer elements etc.) and translational (e.g. start and stop codons) control elements, linked in matching reading frame to the coding sequences.

Any suitable host cell may be used, including prokaryotic and eukaryotic cells and may be selected according to the chosen expression system e.g. bacterial, yeast, insect (e.g. baculovirus-based) or mammalian expression systems. Very many different expression systems are known in the art and widely described in the literature. For example, *E. coli* can be used as host cells for peptide production, in which case, the regulating sequence may comprise, for example, the *E. coli* trp promoter. Other suitable hosts include Gram-negative bacteria other than *E. coli*, Gram-positive bacteria, yeast insect, plant or animal cells e.g. genetically engineered cell-lines.

Expression vectors which comprise the nucleic acid molecules described above constitute a further aspect of the present invention.

Any convenient vector may be used to achieve expression according to the methods of the invention and very many are known in the art and described in the literature. Suitable vectors thus include plasmids, cosmids or virus-based vectors. These vectors, which are introduced into the host cells for expression, are however, preferably plasmid, phage or virus vectors. The vectors may include appropriate control sequences linked in matching reading frame with the nucleic acid molecules of the invention. Other genetic elements e.g. replicons, or sequences assisting or facilitating transfer of the vector into the host cell, stabilising functions, e.g. to assist in maintenance of the vector in the host cell, cloning sites, restriction endonuclease cleavage sites or marker-encoding sequences may be included according to techniques well known in the art. The vectors may remain as discrete entities in the host cell or may, in the case of plasmid insertion vectors or other insertional vectors, be inserted into the host cell chromosome. Random non-specific integration into the host chromosome is possible, although specific homologous integration is preferred. Techniques for this are known in the art (see e.g. Pozzi et al. (1992) J. Res. Microbiol. 143, 449–457 and (1996); Gene 169, 85–90). The integration is "homologous" because the plasmid insertion vector comprises a segment of host cell chromosomal DNA.

Representative exemplary plasmids suitable for expressing genetic constructs, or nucleic acid molecules according to the invention include pTrpBB (Öberg et al., supra) or derivatives thereof. Alternatively such plasmids may be modified to remove sequences encoding the fusion partner if desired. Any high-copy number vector incorporating a Trp-promoter or similar may be used.

A variety of techniques are well known in the art and may be used to introduce such vectors into prokaryotic or eukaryotic cells for expression e.g. bacterial transformation techniques, transfection, electroporation. Transformed or transfected eukaryotic or prokaryotic host cells i.e. host cells containing a nucleic acid molecule according to the invention and as defined above, form a further aspect of the invention.

As described in more detail in the Examples, expression vectors, specifically plasmids, harbouring the nucleic acid molecules of the invention have the advantage of genetic stability in their hosts; no genetic instability was detected in plasmids prepared from cultures grown to high cell densities, as assessed by restriction mapping.

A further aspect of the present invention provides a method for the production of a nucleic acid molecule which encodes a multimeric polypeptide comprising multiple copies of an insulin C-peptide, wherein the expressed multimeric polypeptide is capable of being subsequently cleaved to yield single copies of the insulin C-peptide, said method comprising generating a nucleic acid molecule comprising multiple copies of a nucleotide sequence encoding an insulin C-peptide, linked in matching reading frame.

There are a number of techniques known in the art for generating multimeric copies of a gene or gene fragment which can be used in the methods of the present invention. For example, synthetic DNA fragments can be head-to-tail polymerised utilising designed single-stranded non-palindromic protruding ends. The polymerised DNA fragments can then be directly ligated to matching protrusions resulting from enzymatic restriction (Ljungquist et al. (1989) Eur. J. Biochem. 186, 563–569). Other methods to achieve multimerisation of gene fragments are based on the use of class IIS restriction enzymes such as Bsp MI (Ståhl et. al (1990) Gene 89, 87–193) or Bsm I (Haydn and Mandecki (1988) DNA 7, 571–577). Alternative strategies involve polymerisation of the gene construct and ligation of adapter molecules containing restriction sites to allow further subcloning (Åslund et al. (1987) Proc. Natl. Acad. Sci. USA 84, 1399–1403 and Irving et al. (1988) in Technological Advances in Vaccine Development, A. R. Liss Inc., New York 97–105). Methods for de novo synthesis of genes are also known, involving the use of the polymerase chain reaction (PCR), that would be suitable for the generation of multimeric gene fragments (Majumder (1992) Gene 110, 89–94) and Nguyen et al. (1994) in Advances in Biomagnetic Separation, Eaton Publishing Co., Natick 73–78).

In a preferred embodiment of the method according to the invention, the purified gene fragments (i.e. nucleotide sequences encoding an insulin C-peptide) are allowed to polymerize in a head-to-tail fashion (multimerise), due to designed non-palindromic protrusions and are then ligated into a plasmid digested by a restriction enzyme, preferably Sfi I.

In a particularly preferred embodiment, a plasmid comprising a nucleotide sequence (e.g. a gene fragment) encoding an insulin C-peptide is digested to excise the said sequence origene fragment and after multi-merisation of the sequences or gene fragments they are ligated back into the digested plasmid. Transformants may advantageously be screened using a PCR-screening technique (Ståhl et al. (1993) Biotechniques 14, 424–434) which amplifies the segment encoding one or more copies of the insulin C-peptide. The PCR amplified fragments can be compared by agarose gel electrophoresis. In a further preferred embodiment, gene fragments encoding a desired number of concatamerized insulin C-peptides e.g. three or seven, are isolated and ligated into a further plasmid which has been digested using the same restriction enzyme as was used to excise the fragment encoding the insulin C-peptide. Most preferably, this later plasmid, which will be used for transformation of host cells, additionally comprises a suitable promoter and a sequence encoding a suitable fusion partner for the insulin C-peptide.

Further aspects of the invention include the products of the aforementioned methods, namely an insulin C-peptide multimer and the individual C-peptides released from said multimer by cleavage.

In particular, this aspect of the invention provides a multimeric polypeptide comprising multiple copies of an insulin C-peptide cleavable to release single copies of said insulin C-peptide. Optionally, the multimeric polypeptide may additionally comprise a fusion partner, and/or linker regions comprising a cleavage site flanking each said C-peptide monomer.

Also provided is a method for producing a multimeric polypeptide comprising multiple copies of an insulin C-peptide cleavable to release single copies of said insulin C-peptide, said method comprising culturing a host cell containing a nucleic acid molecule encoding said multimeric polypeptide under conditions whereby said multimeric polypeptide is expressed, and recovering the expressed multimeric polypeptide.

The host cells may be cultured using techniques known in the art e.g. batch or continuous culture formats.

The multimeric gene product. or polypeptide may be recovered from the host cell culture using standard techniques well known in the art, e.g. standard cell lysis, and protein purification techniques. As mentioned above, where a fusion partner is included in the multimeric polypeptide, purification may readily be achieved based on affinity binding of the fusion partner.

A variety of techniques are known in the art for isolating proteins or polypeptides from cells or cell culture medium, both native and recombinantly expressed, and any of these may be used. Cell lysis to release intracellular proteins/polypeptides may be performed using any of the many methods known in the art and described in the literature, and if necessary further purification steps may be performed, again based on techniques known in the art, depending on whether batch or continuous culture methods are used.

Heat treatment methods for the lysis of cells and recovery of polypeptides have been found to be particularly effective in the case of the insulin C-peptide multimeric polypeptides of the present invention, for example the method described in WO90/00200 and modifications thereof. Such methods involve heating the host cell-containing culture medium e.g. for 50–100° C. for a period of time, generally not exceeding 1 hour, whereby the expressed polypeptide is released into the medium, advantageously in substantially pure form. This is believed to result from a selective release of the expressed polypeptide. In particular, it has surprisingly been observed that such a method works well in the case of soluble polypeptide products which are stable to the heat treatment, whether recombinant or not (and the method may thus be of more general applicability), but especially in the case of the insulin C-peptide multimeric polypeptide of the invention, where surprisingly high yields of high purity product may be obtained. Then, for example, such heat treatment may take place by heating at 80–100° C. e.g. 85–99° C. or 90–95° C. for 5–20 minutes, e.g. 8–10 minutes, and cooling thereafter, e.g. to 0–4° C. or on ice.

Following recovery of the multimeric polypeptide, it may be cleaved to release the individual insulin C-peptide monomers. Accordingly a further aspect of the invention provides a method for producing an insulin C-peptide, said method comprising cleaving a multimeric polypeptide as defined above, to release single copies of said insulin C-peptide.

Following cleavage of the multimeric polypeptide as discussed above to yield individual C-peptide monomers, these may also further be purified, e.g. to homogeneity (e.g. as demonstrated by SDS-PAGE) using well known standard techniques of purification e.g. ultrafiltration, size-exclusion chromatography, clarification, reversed-phase chromatography etc.

A further aspect of the present invention is the use in therapy of the cleaved peptide products of the methods described above. The cleaved insulin C-peptide can be used in the treatment of type 1 diabetes and/or diabetic complications. Also within the scope of the a present invention therefore, is a method of treating type 1 diabetes or the complications thereof comprising administration of insulin C-peptide prepared by any of the methods described above.

The invention will now be described in more detail by way of non-limiting Examples and with reference to the following figures in which:

FIG. 1—is a schematic description of the production of gene constructs according to the invention, including the multimerization of the C-peptide-encoding gene fragment.

Figure 2B:
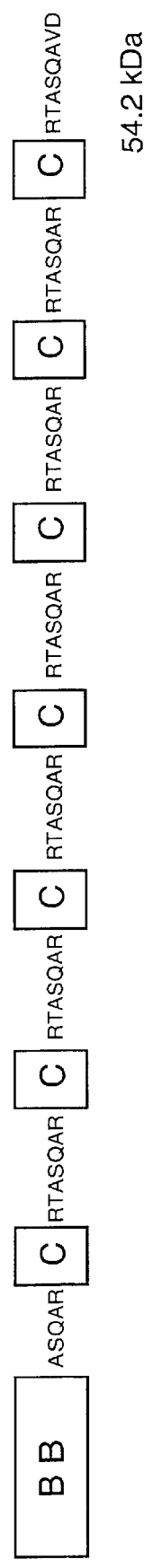

FIGS. 2A and 2B—are schematic descriptions of the to gene products, BB-C3 (A) and BB-C7 (B), with the linker regions flanking the C-peptide indicated in single letter code. Arginine residues (in bold) flank each C-peptide. Exemplary representative linker regions include RTASQAR (SEQ ID NO:2), ASQAR (SEQ ID NO:3), and RTASQAVD (SEQ ID NO:4).

FIG. 2C—shows the amino acid sequence of the C-peptide in single letter code (SEQ ID. NO. 1).

Figure 3:
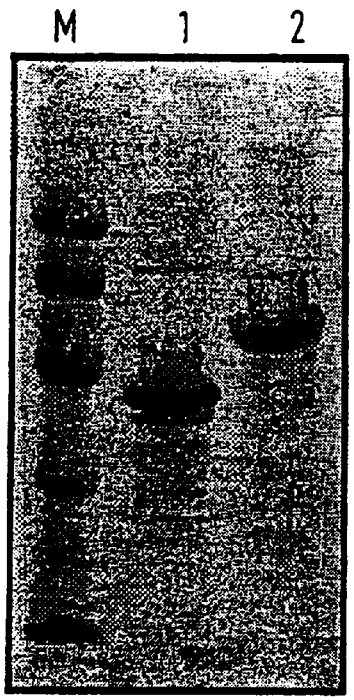

FIG. 3—is a copy of a photograph of an SDS-PAGE (10–15%) gel under reducing conditions of the two fusion proteins BB-C3 (Lane 1) and BB-C7 (Lane 2), respectively, after affinity purification on HSA-Sepharose. Marker proteins with molecular masses of 94, 67, 43, 30, 20 and 14 kDa, respectively appear in Lane M.

Figure 4A:
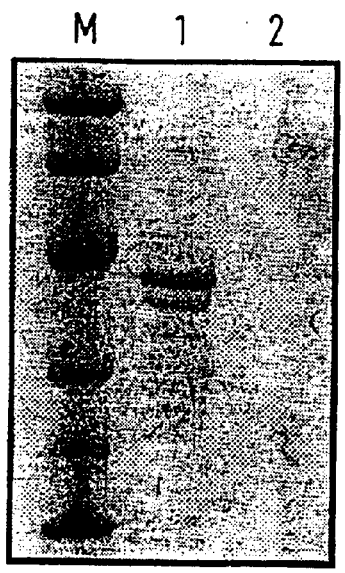

FIG. 4A—is a copy of a photograph of a SDS-PAGE (10–15%) gel under reducing conditions of BB-C3 and after incubation for various times with trypsin and carboxypeptidase B. Lane 1 shows the undigested fusion proteins and lane 2 protein digests after 5 minutes processing with trypsin and carboxypeptidase B. Lane M shows maker proteins with molecular masses of 94, 67, 43, 30, 20 and 14 kDa, respectively.

Figure 4B:
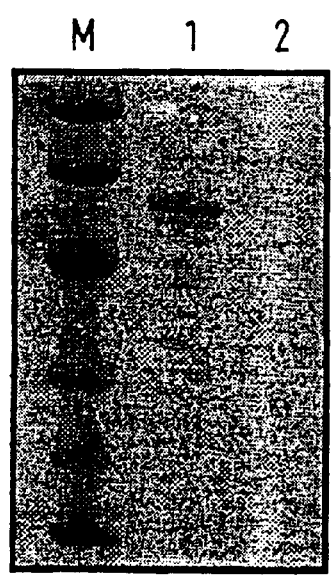

FIG. 4B is as for FIG. 4A, except the fusion product BB-C7 was examined here.

Figure 5:
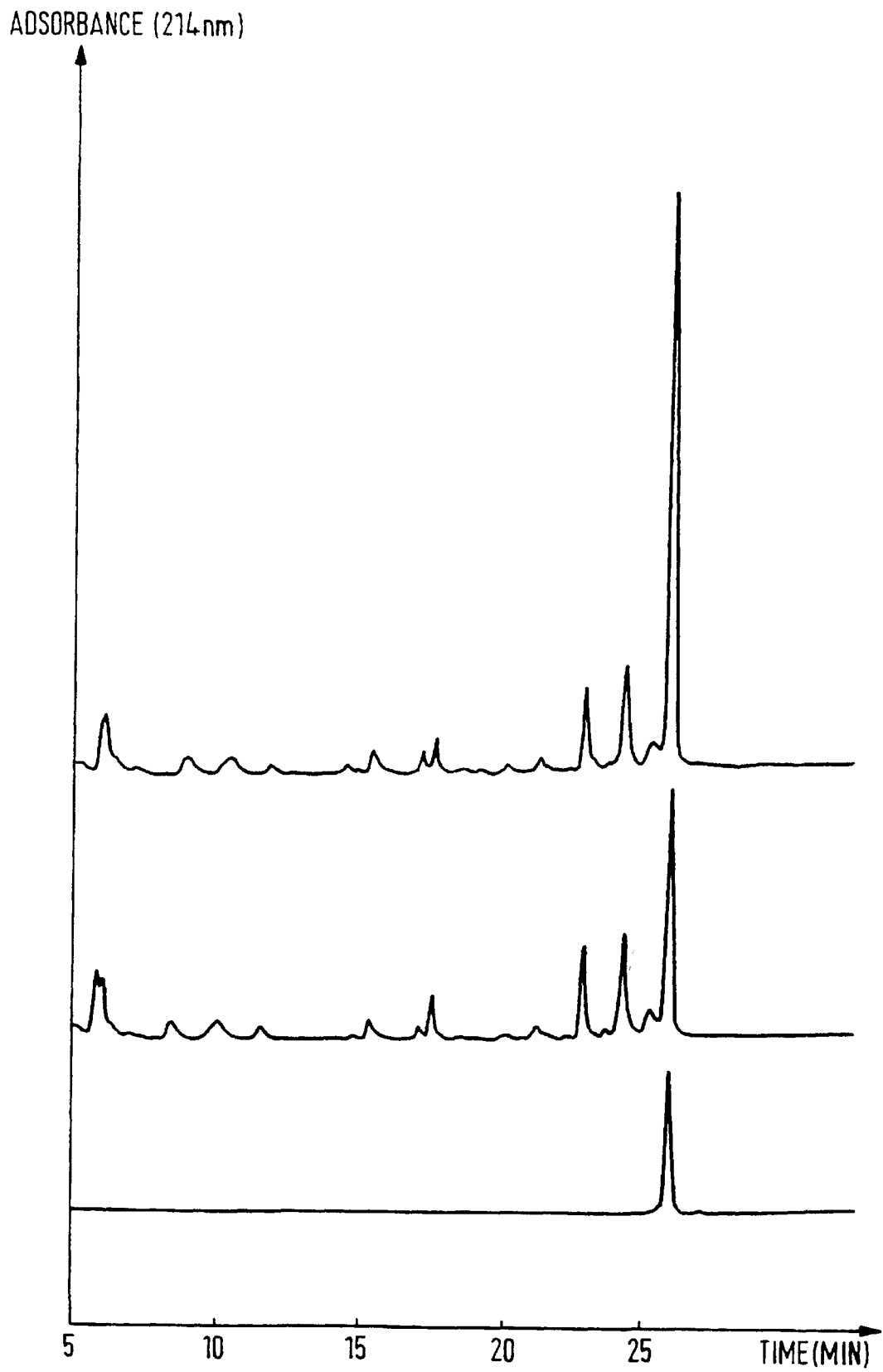

FIG. 5—shows reverse phase chromatography (RPC) analysis of the trypsin and carboxypeptidase B cleavage mixtures from equimolar amounts BB-C7 (upper) and BB-C3 (middle), respectively. Insulin C-peptide from Sigma (lower) was analysed as a control.

Figure 6:
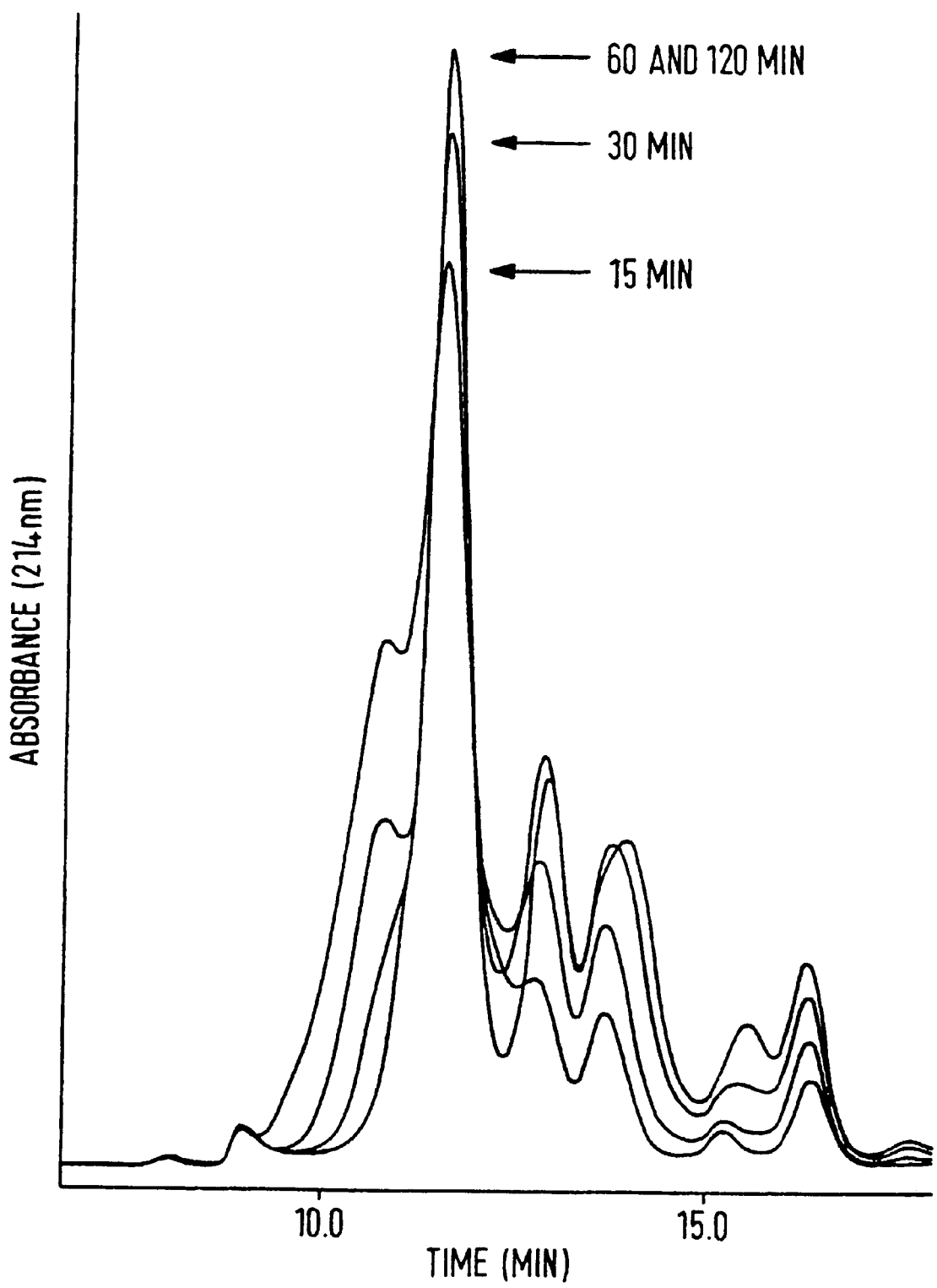

FIG. 6—shows overlay plots of size exclusion chromatograms (Superdex Peptide, Pharmacia Biotech, Uppsala, Sweden) of the BB-C7 fusion product processed for various times with trypsin (mass ratio 5000:1) and carboxypeptidase B (mass ratio 2000:1).

FIG. 7—shows reverse phase chromatography analysis of the insulin C-peptide originating from processed BB-C7(A) by comparison to insulin C-peptide standards provided by Eli Lilly (B) or purchased from Sigma (C).

FIG. 8—illustrates the amino acid sequence in single letter code of the peptide product comprising the fusion partner BB and seven copies of the insulin C-peptide (SEQ ID NO. 5).

Figure 9:
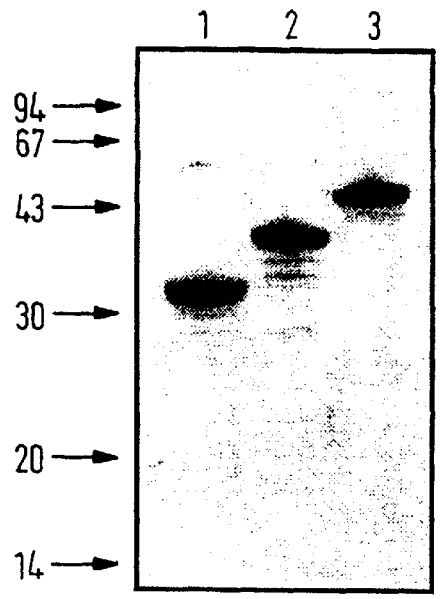

FIG. 9—shows analysis by SDS-10–15% PAGE of the synthesized fusion proteins, BB-Cl (lane 1), BB-C3 (lane 2) and BB-C7 (lane 3), after affinity purification on HSA-Sepharose. Molecular masses are to be indicated in kDa.

Figure 10:
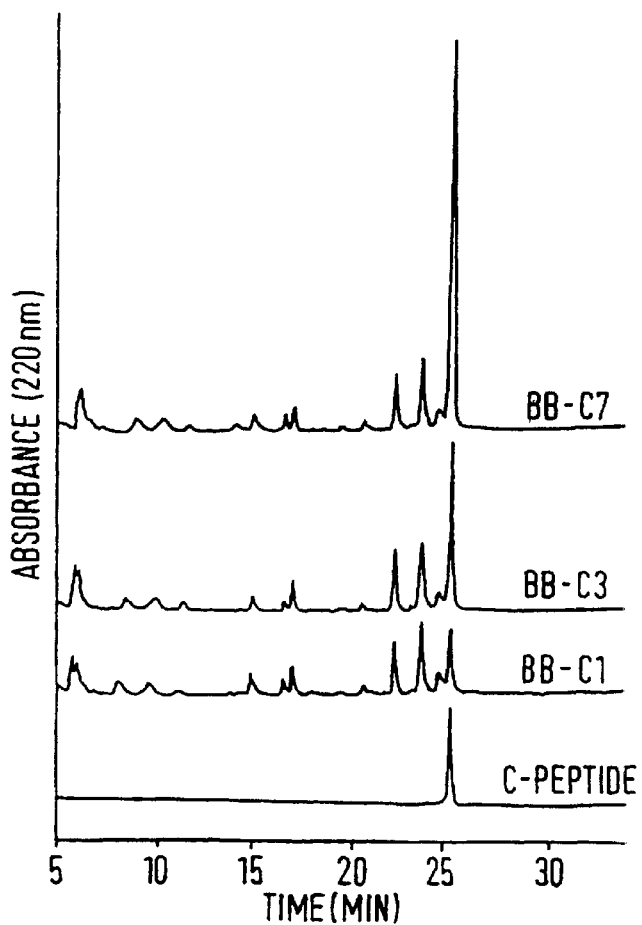

FIG. 10—shows RPC analysis of the trypsin+ carboxypeptidase B cleavage mixtures from equimolar amounts of BB-C1, BB-C3 and BE-C7, respectively. A commercially available C-peptide standard (Sigma) was included as a control (see bottom).

Figure 11:
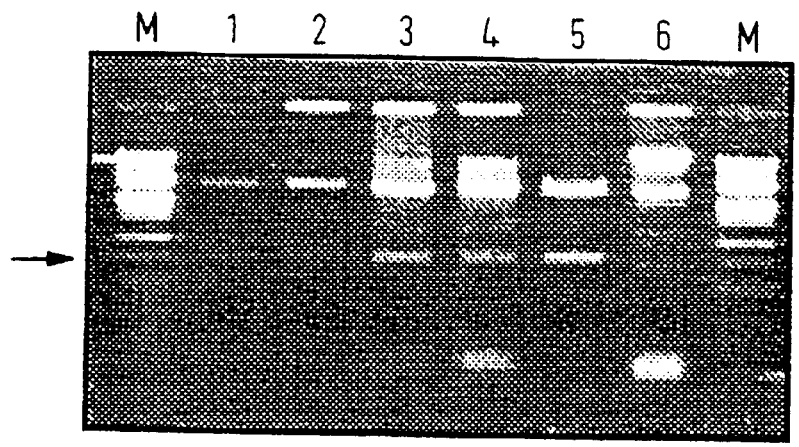

FIG. 11—shows agarose gel (1%) electrophoresis analysis of KpnI-PstI restriction of pTrpBB-C7 plasmid preparations from E. coli cultivations grown for 0 (Lane 1), 7 (Lane 2), 27 (Lane 3) or 31 hours (Lane 4). Lane 5 shows a KpnI-PstI restriction the original pTrpBB-C7 plasmid used for the initial transformation of the E. coli cells and lane 6 uncleaved pTrpBB-C7 after 31 hours of cultivation . The marker (M) lanes contains PstI-restricted: lambda phage DNA. The arrow indicates the position for the C7 fragment.

Figure 12:
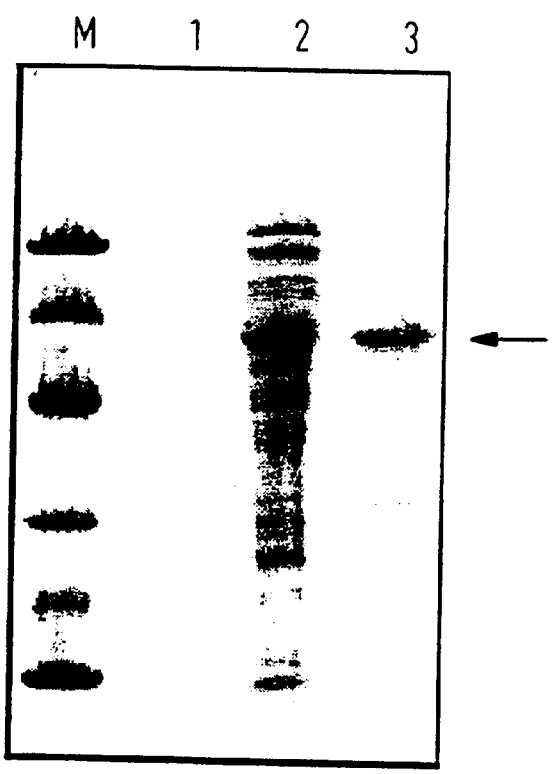

FIG. 12—shows SDS-PAGE analysis (under reducing conditions) of samples from a BB-C7 cultivation. Lane 1: 2 $\mu$l of medium from an untreated culture. Lane 2: 0.5 $\mu$l of sonicated culture. Lane 3: 0.5 $\mu$l of medium after heat treatment of the culture. The arrow indicates the position of the BB-C7 fusion protein. Lane M shows marker proteins of molecular masses of 94, 67, 43, 30, 20 and 14 kDa.

EXAMPLE 1

Preparation of DNA Constructs

The four synthetic oligonucleotides Jope 10(5'- CGGCCTCCCA GGCCCGCGAA GCTGAGGACC TGCAAGTTGG TCAGGTTGAA CTGGGCGGTG GCCCGGGTGC AGGC-3') (SEQ ID,NO. 6), Jope 11 (5'- TCTTTGCAGC CGCTGGCTTT AGAAGGTTCT CTTCAGCGTA CGGCCTCCCA GGCCGTCGAC TAACTGCA-3') (SEQ ID NO. 7), Jope 12 (3'- CATGGCCGGA GGGTCCGGGC GCTTCGACTC CTG- GACGTTC AACCAGTCCA ACTTGACCCG CCACCGGG-5') (SEQ ID NO. 8) and Jope 13 (3'- CCCACGTCCG AGAAACGTCG GCGACCGAAA TCT- TCCAAGA GAAGTCGCAT GCCGGAGGGT CCG- GCAGCTGATTG-5') (SEQ ID NO. 9) were phosphorylated and allowed to anneal pair-wise (Jope 10:Jope 12 and Jope 11:Jope 13) by incubation at 70° C. for 10 min with subsequent cooling to room temperature. The two created linkers were mixed and ligated to KpnI-PstI digested plasmid pUC18 (Yanish-Perron et al., 1985, Gene 33, 103–106) (FIG. 1) and the ligation mixture were transformed to the dcm-*Escherichia coli* strain GM31 (Marinus, (1973) Mol. Gen. Menet. 127,.47–55). A transformant (PUC-Ci) with the correct nucleotide sequence in the inserted insulin C-peptide-encoding gene fragment was identified using PCR-based solid phase DNA sequencing (Hultman et al., (1989) Nucl. Acids Res. 17, 4937–4946). Plasmid DNA from pUC-C1 was prepared and after restriction with SfiI. both the excized insulin C-peptide-encoding gene fragment and the vector part were purified using the Mermaid-kit (glass-milk) (BIO 101 Inc., CA, USA) or the GeneClean-kit (BIO 101 Inc., CA, USA); respectively.

The purified insulin C-peptide gene fragments were allowed to polymerize in a head-to-tail fashion, due to designed non-palindromic protrusions, and were thereafter ligated back to the purified SfiI-digested plasmid. *E. coli* RRIΔM15 cells (Rüther, (1982) Nucl. Acids Res.: 10, 5765–5772) were transformed with the ligation mixture and resulting transformants was screened using a PCR-screening technique (Ståhl et al., (1993) supra). Briefly, single colonies were picked to PCR tubes containing 50 μl PCR reaction mixture (20 mM TAPS, pH 9.3 at 20° C., 2 MrM $MgCl_2$, 50 mM KCl, 0.1% Tween-20, 0.2 umM dNTP, 6 pmole of each primer (RIT27: 5'-GCTTCCGGCTCGTATGTGTG-3' (SEQ ID NO. 10) and RIT28: 5'-AAAGGGGGATGTGCTGCAAG GCG-3') (SEQ ID NO. 11)vand 1.0 unit of Taq polymnerase). The two PCR primers RIT27 and RIT28 have annealing sites in pUC18 flanking the insertion point for the insulin C-peptide fragments. The PCR amplified fragments from clones with different. number of inserted oligonucleotides were compared, with pUC18 as a reference, by agarose gel electrophoresis and transformants could be identified carrying one to seven inserts. The resulting plasmids were thus denoted pUC-C1, pUC-C2 etc.

Plasmids were prepared and gene fragments containing the desired number of inserts were excized by KpnI-PstI digestion. Gene fragments encoding one, three or seven concatamerized insulin C-peptides, respectively, were isolated and ligated to similarly digested pTrpBBTIT2, and the resulting plasmids were denoted pTrpBB-C1, pTrpBB-C3 and pTRpBB-C7, respectively. Plasmid pTrpBBT1T2 was constructed from plasmid pTrpBB (Öberg et al., (1994) in Proc. 6th Eur. Congress Biotechnol; Elsevier Science B. V. 179–182) by insertion of a transcription terminator sequence derived from plasmid pKK223-3 (Pharmacia Biotech, Uppsala, Sweden). The transcription terminator sequence was obtained from pKK223-3 using a standard PCR amplification protocol (Hultman et al., (1989) supra) and the oligonucleotides HEAN-19,5'-CCCCCTGCAGCTCGAGCGCCTTTA ACCTGTTTTGGCGGATG-3' (SEQ ID NO. 12) and HEAN-20, 5'CCCCAAGCTTAGAGTTTGTAG AAACGC-3' (SEQ ID NO. 13).

The restriction sites introduced by PCR were digested with PstI and HindIII, followed by insertion into pTrpBB, previously digested with the same enzymes. The resulting expression vector pTrpBBT1T2 encodes an affinity handle consisting of a trp operon-derived leader sequences (eight amino acids) and a serum albumin binding region BB (25 kDa) (Nygren et al., (1988) supra) derived from streptococcal protein G. Transcription is under control of the *E. coli* trp promoter. In addition, the plasmid carries the gene for kanamycin resistance.

EXAMPLE 2

Protein Expression and Purification

*E. coli* cells harbouring pTrpBB-C3 and pTrpBB-C7, and thus encoding the fusion proteins BB-C3 and BB-C7, respectively, were grown overnight at 37° C. in shake-flasks containing 10 ml Tryptic Soy Broth (Difco, USA) (30 g/l) supplemented with yeast extract (Difco) (5 g/l) and kanamycin monosulfate (50 mg/l). The overnight cultures were diluted 10-fold to 100 ml into baffled shake-flasks having the same type of media and grown at 37° C. Gene expression was induced at mid-log phase ($A_{600}$ nm≅1) by the addition of β-indole acrylic acid to 25 mg/l. Cells were harvested 20 hours after induction, by centrifugation at approximately 6000 g for 10 min. Cells were resuspended in 1/20 of the culture volume in TST (50 mM Tris-HCl pH 8.0. 200 mM NaCl, 0.05% Tween 20, 1 mM EDTA), lysed by sonication and centrifuged at approximately 40,000 g. The samples for the sonication were prepared by sedimenting the shake-flask culture by centrifugation, and thereafter resuspending the cells in 30 ml of cold TST buffer. The samples were stored on ice during a 2 minute pulsed sonication which was performed on a Sonics and Materials Inc. (Danbury, Conn. USA) Vibra Cell (500 W) using a 13 mm standard horn tip, a 70% duty cycle (20 kHz) and with the output control set to 6.5. The supernatants, containing soluble cytoplasmic proteins, were filtered (0.45 μm) and diluted to 100 ml with TST. The soluble fusion proteins were isolated by affinity chromatography on human-serum-albumin (HSA)-Sepharose (Nygren et al., (1988) supra) as described by Stahl et al (1989) J. Immunol. Meth. 124, 43–52. Eluted fractions were monitored for protein content by absorbance measurement at 280 nm and relevant fractions were lyophilised.

FIG. 3 shows affinity purified BB-C3 and BB-C7, V respectively, after a single step purification on HSA-Sepharose. Full-length products were predominant for both fusion proteins which also migrated in accordance with their molecular masses; 39.1 and 54.2 kDa, respectively. The expression levels for shake-flask cultivations were almost identical for the two fusion proteins; being 130 mg/l for BB-C3 and 120 mg/l for BB-C7.

EXAMPLE 3

Proteolytic Digestion of the Fusion Proteins

Trypsin, which cleaves C-terminally of basic amino acid residues, has been used for a long time to cleave fusion proteins. Despite expected low specificity, trypsin has been shown to be useful for specific cleavage of fusion proteins, leaving basic residues within folded protein domains uncleaved (Wang et al., (1989) J. Biol. Chem. 264, 21116–21121). Trypsin has the additional advantages of being inexpensive and readily available. Here we have used trypsin in combination with carboxypeptidase B for the processing of BB-C3 and BB-C7, respectively, in order to obtain native human insulin C-peptide. Trypsin would thus cleave the fusion. proteins C-terminally of each arginine residue and; carboxypeptidase B would remove the C-terminal arginine present on each insulin C-peptide monomer after trypsin digestion.

To analyze the efficiency of the processing, the two fusion proteins, BB-C3 and BB-C7 were incubated with trypsin and carboxypeptidase B for various times and subjected to SDS/PAGE analysis. It was found that both fusion proteins were processed rapidly and after 5 minutes processing, no fusion protein could be visualized by the SDS/PAGE analysis (FIGS. 4A and B).

In addition, an analysis was performed to compare the relative yields of insulin C-peptide monomers after cleavage of the fusion proteins BB-C3 and BB-C7, respectively. The cleavage mixtures after trypsin and carboxypeptidase B treatment of equimolar amounts of BB-C3 and BB-C7, respectively, were analysed by reverse phase HPLC (250 mm, Kromasil C8 column, 4.6 mm inner diameter, particle size 7 μm, Hewlett Packard 1090).

Elution was performed using a .10–40% acetonitrile gradient containing 0.1% trifluoroacetic acid during 30 minutes at 40° C. As can be seen in FIG. 5, a significantly higher ratio between the insulin C-peptide product (elution time ca. 25.4 min) and other cleavage products (of BB fusion partner origin) was obtained from cleavage of the BB-C7 fusion protein compared to cleavage of the BB-C3 fusion protein. Integration of the insulin C-peptide peak areas (C7:C3) gave a peak area ratio of 2.43, close to the theoretical 2.33.

This does not give any information about when the fusion proteins are completely processed. To investigate when the trypsin-carboxypeptidase B treatment has reached completion, the fusion protein, BB-C7 was subjected to enzymatic processing for various times. The lyophilized. BB-C7 fusion protein was dissolved in 100 mM phosphate buffer, pH 7.5, containing 0.1% (by vol.) Tween 20 to a protein concentration of 1 mg/ml, respectively, Trypsin (T-2395, Sigma, St. Louis, Mo., USA) and carboxypeptidase B (Boehringer Mannheim) were added to trypsin/fusion protein ratios of 1/5000 (by mass) and carboxypeptidase B/fusion protein ratios of 1/2000 (by mass), respectively. After 15, 30, 60 and 120 minutes, samples were taken from the cleavage mixtures and the digestions were stopped by decreasing the pH to 3 by adding HAc. Acetonitrile to 20% (by vol.) was added in order to stabilize the cleavage products.

The cleavage material was analyzed by size-exclusion chromatography (Superdex Peptide column on SMART™ system, Pharmacia Biotech, Uppsala, Sweden) and by making overlay plots of the chromatograms (FIG. 6), it could be concluded that BB-C7 was completely processed after 60 minutes under these conditions since no additional insulin C-peptide was obtained by increased incubation times. These results also indicate that it would be possible to obtain quantitative yields of insulin C-peptide from fusion proteins comprising multimeric forms of insulin C-peptide.

EXAMPLE 4

Characterization of the Obtained Insulin C-peptide: Reversed Phase Chromatography (RPC) and Mass Spectrometry In order to confirm that the obtained peptide really corresponds to native human insulin C-peptide, two different analyses were performed. Firstly, reversed phase chromatography (RPC) analysis was used for comparison of RPC-purified insulin C-peptide obtained by processing of BB-C7 to insulin C-peptide standards, said standards being C-peptide obtained from Eli Lilly (CA, USA) and commercially available insulin C-peptide fragment 3-33 (Sigma, USA). The insulin C-peptide preparations were analyzed by RPC on a Sephasil C8 5 μm SC2. 1/10 column using the SMART system (Phairmacia Biotech, Uppsala, Sweden). Elution was performed using a gradient of 26–36% acetonitrile containing 0.1% (by vol.) trifluoroacetic acid during 20 min at 25° C. The flow rate was 100 μl/min and the absorbance was measured at 214 nm. It could be concluded that all three preparations were close to identical, having the same retention time and the same low level of impurities (FIG. 7). Secondly, the insulin C-peptide obtained from BB-C7 was subjected to mass spectrometry (Table 1). The protein mass determination was performed using a JEOL GX102 mass spectrometer (JEOL, Japan)) equipped with an electrospray unit. The good agreement in mass (Table 1), together with the observed similarities to insulin C-peptide standards in the comparative RPC analysis, suggest that native human insulin C-peptide was obtained.

TABLE 1

| Molecular mass of insulin C-peptide (Da) | |
|---|---|
| Calculated | 3020.3 |
| Experimental | 3019.7 ± 1.8 |

EXAMPLE 5

Characterization of the Obtained Insulin C-peptide Monomer: Radioimmunoassay (RIA)

The insulin C-peptide monomer obtained from cleavage of the fusion protein BB-C7 was analyzed using a commercially available radioimmunoassay developed to monitor human insulin C-peptide levels in e.g. blood and urine (Euro-Diagnostica, Malmö, Sweden; cat. no. MD 315). For comparison, also a preparation of insulin C-peptide (Eli-Lilly Co, Indianapolis, Ind, USA), previously demonstrated to be biologically active (Johansson et al., (1992) Diabetologia 35:1151–1158), was analyzed. Samples for analysis were prepared by weighing followed by dilution to final concentrations of 3.31 and 3.30 nanomoles/liter of the two preparations of C-peptide, respectively, in 0.05 M Na-phosphate buffer, pH 7.4, 5% human albumin serum (HSA) and 0.02% Thimerosal. Briefly, the assay involves a rabbit anti-human C-peptide antiserum, $^{125}$I-human insulin C-peptide tracer, a goat anti-rabbit Ig antiserum-PEG reagent, human insulin C-peptide standards and control samples for quantification of insulin C-peptide in assayed samples after the construction of a standard curve. The results from the analysis of the two samples are summarized in Table 2 below. The results show that the two preparations are equally recognized and quantified using the RIA assay.

TABLE 2

Comparative RIA analysis of insulin C-peptide with demonstrated biological activity and insulin C-peptide obtained from cleavage of the recombinant fusion protein BB-C7.

| Sample | Expected concentration (nM) | Assayed concentration (nM) |
|---|---|---|
| Insulin C-peptide 2.34 (71%) (from cleavage of fusion protein BB-C7) | | 3.31 |
| Insulin C-peptide 2.41 (73%) (from Eli-Lilly) | | 3.30 |

EXAMPLE 6

Expression, Purification and Proteolytic Digestion of Fusion Proteins BB-C1, BB-C3 and BB-C7

This Example presents additional comparative results regarding the BB-C1 fusion protein, for the experiments presented in Examples 2 and 3.

E. coli cells harbouring plasmids pTrp BB-C1, pTrp BB-C3 or pTrp BB-C7 respectively (see Example 1) were grown, and the fusion proteins were expressed, obtained, purified and analysed as described in Example 2.

Analysis of E. coli cells transformed with either pTrp BB-C1, pTrp BB-C3 or pTrp BB-C7 showed that the encoded fusion proteins, BB-C1, BB-C3 and BB-C7 accumulated intracellularly as soluble gene products (data not shown). After cell disruption, the produced fusion proteins were efficiently purified by HSA-affinity chromatography. FIG. 9 shows the affinity purified BB-C1, BB-C3 and BB-C7 fusion proteins, respectively, after a single step purification on HSA-Sepharose. Full-length products were predominant for the three fusion proteins, which also migrated in accordance to their molecular masses; 31.5, 39.1 and 54.2 kDa, respectively. The expression levels for shake-flask cultures were reproducible and similar for the three different fusion proteins, in the range of 40–60 mg/l.

To analyse the efficiency of the processing of the three affinity-purified fusion proteins, BB-C1, BB-C3 and BB-C7 were incubated with trypsin and carboxypeptidase B for various times and subjected to SDS-PAGE analysis. The three fusion proteins were processed rapidly, and after 5 minutes of treatment, no remaining full-length fusion protein was detected by the SDS-PAGE (data not shown).

Efficiency of proteolytic processing was further analysed as described in Example 3, and it was found that BB-C7 was completely cleaved after 60 minutes.

In order to compare more adequately the relative yields of C-peptide monomers after cleavage of the BB-C1, BB-C3 and BB-C7 fusion proteins, respectively, a reverse phase HPLC analysis was performed (as described in Example 3). The cleavage mixtures from a 120 minute trypsin+ carboxypeptidase B treatment of approximately equimolar amounts of BB-C1, BB-C3 and BB-C7, respectively, were analysed. (The $A_{220\ nm}$ was monitored). Results (FIG. 10) demonstrated a significantly higher ratio between the C-peptide product and other cleavage products of the BB-C7 and BB-C3 fusion proteins, as compared to cleavage of the BB-C1 fusion protein. Approximately equimolar amounts of each fusion protein were loaded on the RPC column, as demonstrated by the equal peak heights originating from trypsin-digested BB-tag visible in the three: chromatograms (FIG. 10). Integration of the C-peptide peak areas (940, 2324 and 5647 absorbance units×s×$10^{-3}$ for BB-C1, BB-C3 and BB-C7 respectively) resulted in ratios of 2.5 for C3:C1 and 6.0 for C7:C1, being close to the theoretical values 3 and 7, respectively.

The results further show an improved yield of insulin C-peptide monomers from insulin C-peptide multimers (C3, C7) as compared with a monomeric fusion protein (C1).

EXAMPLE 7

Investigation of Genetic Stability for the Plasmid pTrpBB-C7 Encoding the BB-C7 Fusion Protein This example describes how the genetic stability for the plasmid pTrpBB-C7 encoding the BB-C7 fusion protein was assessed. E. coli cells harbouring plasmid pTrpBB-C7 were grown for different times and samples were taken after 0, 7, 27 and 31 hours of cultivation. Thirty-one hours would resemble a cultivation time for a large-scale fermentation production of BB-C7. Plasmids were recovered from the samples according to standard protocols (Sambrook et al., A Laboratory Manual, Second Edition, Cold Spring Harbor Laboratory Press, New York). The plasmids were subjected to KpnI-PstI restriction, in order to excize the fragment encoding the C7 concatamer (see FIG. 1). The original pTrpBB-C7 plasmid used for the initial transformation of the E. coli cells was included as control, and was thus also subjected to KpnI-PstI restriction. As can be seen in FIG. 11, the restricted fragment has the same size from all samples, verifying that the plasmid pTrpBB-C7 would be genetically stable during cultivations for extended times.

EXAMPLE 8

Heat Treatment for Selective Release of BB-C7 into the Culture Medium

This example describes how the BB-C7 fusion protein could be released into the culture medium by heat treatment and thereby significantly improve the purity of the starting material for further purification of BB-C7. Background: Compared to the most widely used method for releasing, recombinant proteins produced intracellularly in E. coli (including the unit operations centrifugation, resuspension of the cell pellet in a appropriate buffer and cell disruption by high pressure homogenisation), the release of the gene product by the heat treatment method have many advantages: (i) a production scheme including the heat treatment have one clarification step less, (ii) the stability of the gene product increases due to heat denaturation of host cell proteases, (iii) a significant. initial purification of the gene product is obtained by the precipitation of other E. coli proteins and, (iv) the release of nucleic acids is reduced compared to a total disruption of the cells. The method would be suitable also for release of other intracellularly expressed recombinant proteins that are soluble also at high expression levels and that are stable to the heat treatment required to release the protein.

E. coli cells harbouring plasmid pTrpBB-C7, encoding BB-C7, were cultivated as described in Example 2. As an alternative to the described sonication process (Example 2) for cell disrupture, a heat treatment step could be utilized for a selective and efficient release of BB-C7 into the culture medium. The culture was at the end. of the cultivation submerged into a water bath with boiling water for 8–10 minutes. The culture had after this time reached a temperature of approximately 90° C. The shake-flask was thereafter placed on ice. As can be seen in FIG. 12 (lane 3), at this temperature, the BB-C7 fusion protein is released into the culture medium without release of substantial amounts of host proteins. The host proteins are most likely completely denatured by this treatment. In contrast, sonication (FIG. 12, lane 2) and other mechanical methods for cell disrupture would release also all host proteins as well as nucleic acids, resulting in a very heteregenous starting material for further purification of BB-C7. Very little protein is normally secreted by the E. coli culture (FIG. 12, lane 1). The BB-C7 was found to be stable to the heat treatment and could be further purified and processed for release of C-peptide monomers as described in Examples 1–3.

What is claimed is:

1. A nucleic acid molecule comprising multiple copies of a nucleotide sequence encoding an insulin C-peptide of SEQ ID NO:1, wherein said nucleic acid molecule encodes a multimeric polypeptide capable of being cleaved to yield single copies of said insulin C-peptide.

2. An expression vector comprise a nucleic acid molecule as defined in claim 1.

3. The expression vector according to claim 2, said expression vector being a plasmid.

4. The expression vector according to claim 3, wherein said expression vector is based on plasmid pTrpBB (SEQ ID NO:14).

5. A host cell containing a nucleic acid molecule as defined in claim 1.

6. The nucleic acid molecule according to claim 1, wherein said multiple copies of said insulin C-peptide or said nucleotide sequence encoding an insulin C-peptide are arranged in tandem.

7. A The nucleic acid molecule according to claim 1, wherein said multimeric polypeptide comprises 2 to 30 copies of said insulin C-peptide.

8. The nucleic acid molecule according to claim 1, wherein said multimeric polypeptide comprises 3 to 7 copies of said insulin C-peptide.

9. The nucleic acid molecule according to claim 1, wherein said multimeric polypeptide further comprises a fusion partner.

10. The nucleic acid molecule according to claim 9, wherein said fusion partner is an affinity binding partner or a ligand.

11. The nucleic acid molecule according to claim 10, wherein said fusion partner is a 25 kDa serum albumin binding region (BB) derived from streptococcal protein G.

12. The nucleic acid molecule according to claim 1, wherein each insulin C-peptide in said multimeric polypeptide is flanked by linker regions comprising a cleavage site.

13. The nucleic acid molecule according to claim 12, wherein said cleavage site is cleavable by a proteolytic enzyme.

14. The nucleic acid molecule according to claim 13, wherein said cleavage site comprises arginine residues for cleavage by trypsin and carboxypeptidase B.

15. The nucleic acid molecule according to claim 1, wherein said multiple copies of said insulin C-peptide are in matching reading frame.

16. The nucleic acid molecule according to claim 1, wherein said nucleic acid molecule further comprises one or more regulatory or expression control sequences.

17. An expression vector comprising a nucleic acid molecule as defined in claim 16.

18. The expression vector according to claim 17, said expression vector being a plasmid.

19. The expression vector according to claim 18, wherein said expression vector is based on plasmid pTrpBB (SEQ ED NO:14).

20. A host cell containing a nucleic acid molecule as defined in claim 16.

21. A multimeric polypeptide comprising multiple copies of an insulin C-peptide of SEQ ID NO:1, wherein said multimeric polypeptide can be cleaved to release single copies of said insulin C-peptide.

22. A method of producing an insulin C-peptide of SEQ ID NO:1, said method comprising cleaving a multimeric polypeptide as defined in claim 21.

23. The multimeric polypeptide according to claim 21, wherein said multiple copies of said insulin C-peptide are arranged in tandem.

24. The multimeric polypeptide according to claim 21, wherein said multimeric polypeptide comprises 2 to 30 copies of said insulin C-peptide.

25. The multimeric polypeptide according to claim 21, wherein said multimeric polypeptide comprises 3 to 7 copies of said insulin C-peptide.

26. The multimeric polypeptide according to claim 21, wherein said multimeric polypeptide further comprises a fusion partner.

27. The multimeric polypeptide according to claim 26, wherein said fusion partner is an affinity, binding partner or a ligand.

28. The multimeric polypeptide according to claim 27, wherein said fusion partner is a 25 kDa serum albumin binding region (BB) derived from streptococcal protein G.

29. The multimeric polypeptide according to claim 21, wherein each insulin C-peptide in said multimeric polypeptide is flanked by linker regions comprising a cleavage site.

30. The multimeric polypeptide according to claim 29, wherein said cleavage site is cleavable by a proteolytic enzyme.

31. The multimeric polypeptide according to claim 30, wherein said cleavage site comprises arginine residues for cleavage by trypsin and carboxypeptidase B.

32. A method of producing a multimeric polypeptide which contains multiple copies of an insulin C-peptide of SEQ ID NO:1 and can be cleaved to release single copies of said insulin C-peptide, said method comprising culturing a host cell containing a nucleic acid molecule encoding said multimeric polypeptide under conditions whereby said multimeric polypeptide is expressed, and recovering the expressed multimeric polypeptide.

33. The method according to claim 32, wherein said multiple copies of said insulin C-peptide are arranged in tandem.

34. The method according to claim 32, wherein said multimeric polypeptide comprises 2 to 30 copies of said insulin C-peptide.

35. The method according to claim 32, wherein said multimeric polypeptide comprises 3 to 7 copies of said insulin C-peptide.

36. The method according to claim 32, wherein said multimeric polypeptide further comprises a fission partner.

37. The method according to claim 36, wherein said fusion partner is an affinity binding partner or a ligand.

38. The method according to claim 37, wherein said fusion partner is a 25 kDa serum albumin binding region (BB) derived from streptococcal protein G.

39. The method according to claim 32, wherein each insulin C-peptide in said multimeric polypeptide is flanked by linker regions comprising a cleavage site.

40. The method according to claim 39, wherein said cleavage site is cleavable by a proteolytic enzyme.

41. The method according to claim 40, wherein said cleavage site comprises arginine residues for cleavage by trypsin and carboxypepridase B.

* * * * *